United States Patent
Maruyama et al.

(10) Patent No.: US 10,132,755 B2
(45) Date of Patent: Nov. 20, 2018

(54) SURFACE-ENHANCED RAMAN SCATTERING ELEMENT, AND METHOD FOR MANUFACTURING SURFACE-ENHANCED RAMAN SCATTERING ELEMENT

(71) Applicant: HAMAMATSU PHOTONICS K.K., Hamamatsu-shi, Shizuoka (JP)

(72) Inventors: Yoshihiro Maruyama, Hamamatsu (JP); Katsumi Shibayama, Hamamatsu (JP); Masashi Ito, Hamamatsu (JP); Toru Hirohata, Hamamatsu (JP); Hiroki Kamei, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/420,546

(22) PCT Filed: Aug. 9, 2013

(86) PCT No.: PCT/JP2013/071709
§ 371 (c)(1),
(2) Date: Feb. 9, 2015

(87) PCT Pub. No.: WO2014/025038
PCT Pub. Date: Feb. 13, 2014

(65) Prior Publication Data
US 2015/0233832 A1    Aug. 20, 2015

(30) Foreign Application Priority Data

Aug. 10, 2012 (JP) ................................. 2012-178765
Jul. 5, 2013 (JP) ................................. 2013-142165

(51) Int. Cl.
*G01N 21/65*    (2006.01)

(52) U.S. Cl.
CPC ..... *G01N 21/658* (2013.01); *G01N 2021/651* (2013.01)

(58) Field of Classification Search
CPC ....................... G01N 21/658; G01N 2021/651
See application file for complete search history.

(56) References Cited

U.S. PATENT DOCUMENTS

| 9,127,984 B2 | 9/2015 | Tseng et al. |
| 2004/0023046 A1* | 2/2004 | Schlottig ............... G01J 3/44 428/469 |

(Continued)

FOREIGN PATENT DOCUMENTS

| CN | 101281133 | 10/2008 |
| CN | 101319994 | 12/2008 |

(Continued)

OTHER PUBLICATIONS

"Q-SERS™ G1 Substrate," Opto Science, Inc. (retrieved on-line on Jul. 5, 2013).

(Continued)

*Primary Examiner* — Dominic J Bologna
(74) *Attorney, Agent, or Firm* — Drinker Biddle & Reath LLP

(57) ABSTRACT

A SERS element 2 comprises a substrate 21 having a front face 21a; a fine structure part 24, formed on the front face 21a, having a plurality of pillars 27; a first conductor layer 31 formed on the front face 21a and fine structure part 24 so as to cover the front face 21a and fine structure part 24 continuously; and a second conductor layer 32 formed on the first conductor layer 31 so as to form a plurality of gaps G1, G2 for surface-enhanced Raman scattering; while the first and second conductor layers 31, 32 are constituted by the same material.

11 Claims, 13 Drawing Sheets

(56) References Cited

U.S. PATENT DOCUMENTS

| | | |
|---|---|---|
| 2006/0146323 A1 | 7/2006 | Bratkovski et al. |
| 2006/0225162 A1 | 10/2006 | Yi |
| 2008/0094621 A1 | 4/2008 | Li et al. |
| 2008/0218761 A1 | 9/2008 | Nishikawa et al. |
| 2010/0019355 A1* | 1/2010 | Kamins .......... B82Y 10/00 257/627 |
| 2011/0027901 A1 | 2/2011 | Gaster et al. |
| 2011/0116089 A1 | 5/2011 | Schmidt et al. |
| 2011/0166045 A1* | 7/2011 | Dhawan .......... B82Y 10/00 506/39 |
| 2011/0267607 A1 | 11/2011 | Hu et al. |
| 2012/0081703 A1 | 4/2012 | Moskovits et al. |
| 2012/0309080 A1 | 12/2012 | Cunningham et al. |
| 2014/0043605 A1* | 2/2014 | Tseng .......... G01N 21/658 356/301 |
| 2014/0045209 A1* | 2/2014 | Chou .......... G01N 21/6452 435/34 |
| 2014/0154668 A1 | 6/2014 | Chou et al. |
| 2015/0211999 A1 | 7/2015 | Maruyama et al. |
| 2015/0212002 A1 | 7/2015 | Ito et al. |
| 2015/0212003 A1 | 7/2015 | Shibayama et al. |
| 2015/0219562 A1 | 8/2015 | Shibayama et al. |
| 2015/0233832 A1 | 8/2015 | Maruyama et al. |
| 2015/0233833 A1 | 8/2015 | Shibayama et al. |
| 2015/0338346 A1 | 11/2015 | Chou et al. |

FOREIGN PATENT DOCUMENTS

| | | |
|---|---|---|
| CN | 101529229 | 9/2009 |
| CN | 102282094 | 12/2011 |
| CN | 102348966 | 2/2012 |
| CN | 102483354 | 5/2012 |
| JP | H05-044867 U | 6/1993 |
| JP | H07-260646 A | 10/1995 |
| JP | 2003-026232 A | 1/2003 |
| JP | 2005-337771 A | 12/2005 |
| JP | 2007-530925 A | 11/2007 |
| JP | 2007-538264 A | 12/2007 |
| JP | 2008-519254 A | 6/2008 |
| JP | 2008-196992 A | 8/2008 |
| JP | 2008-268059 A | 11/2008 |
| JP | 2009-025316 A | 2/2009 |
| JP | 2009-047623 A | 3/2009 |
| JP | 2009-103643 A | 5/2009 |
| JP | 2009-222507 A | 10/2009 |
| JP | 2009-236830 A | 10/2009 |
| JP | 2009-544967 A | 12/2009 |
| JP | 2010-506191 A | 2/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011-141265 A | 7/2011 |
| JP | 2011-215021 A | 10/2011 |
| JP | 2012-233707 A | 11/2012 |
| TW | 201410591 | 3/2014 |
| WO | WO-2007/149120 A2 | 12/2007 |
| WO | WO-2010/050203 A1 | 5/2010 |
| WO | WO-2010/090111 A1 | 8/2010 |
| WO | WO-2011/021085 A2 | 2/2011 |
| WO | WO-2011/040504 A1 | 4/2011 |
| WO | WO-2012/024006 A2 | 2/2012 |
| WO | WO 2013/015810 | 1/2013 |
| WO | WO-2014/025033 A1 | 2/2014 |
| WO | WO-2014/025034 A1 | 2/2014 |

OTHER PUBLICATIONS

Masahiro Yanagisawa, "Detection of Trace Organic Gas Using Molecular Sensor with Plasmon Antenna," Green Technology, Vo. 22, No. 6, Jun. 10, 2012, pp. 42-47, including at least partial English-language translation.

U.S. Office Action dated Dec. 14, 2015 that issued in U.S. Appl. No. 14/420,422 including double patenting rejections at pp. 8-11.

U.S. Office Action dated Apr. 22, 2016 that issued in U.S. Appl. No. 14/420,502 including Double Patenting Rejections on pp. 2-8.

U.S. Office Action dated Oct. 14, 2016 that issued in U.S. Appl. No. 14/420,510 including Double Patenting Rejections on pp. 2-14.

K. Nakamoto et al., "Arrays of Metallic Nanopillars in Holes for Plasmonic Devices", Retrieved from the Internet: URL: http: http://www.rsc.images/LOC/2011/PDFs/Papers/596_0021.pdf, Oct. 6, 2011, XP055289892.

M. Tomohiko et al., "New localized surface plasmon resonance sensor utilizing nanoimprinting technology", NSTI Nanotechnology Conference and Trade Show-NSTI Nanotech, vol. 1, May 11, 2006, p. 58-p. 61, XP009098538.

W. D. Li et al., "Three Dimensional cavity nanoantenna coupled plasmonic nanodots for ultrahigh and uniform surface-enhanced Raman scattering over large area", Optics Express, vol. 19, No. 5, Feb. 14, 2011, p. 3925-3936, XP002751299.

W. Zhang et al., "Giant and uniform fluorescence enhancement over large areas using plamonic nanodots in 3D resonant cavity nanoantenna by nanoimprinting", Nanotechnology, vol. 23, No. 22, May 10, 2012, p. 225301, XP020224099.

S. M. Wells et al., "Efficient disc on pillar substrates for surface enhanced Raman Spectroscopy", Chemical Communications—Chemcom, vol. 47, No. 13, Jan. 1, 2011, p. 3814-p. 3816, XP055289549.

* cited by examiner

Fig.6
(a)
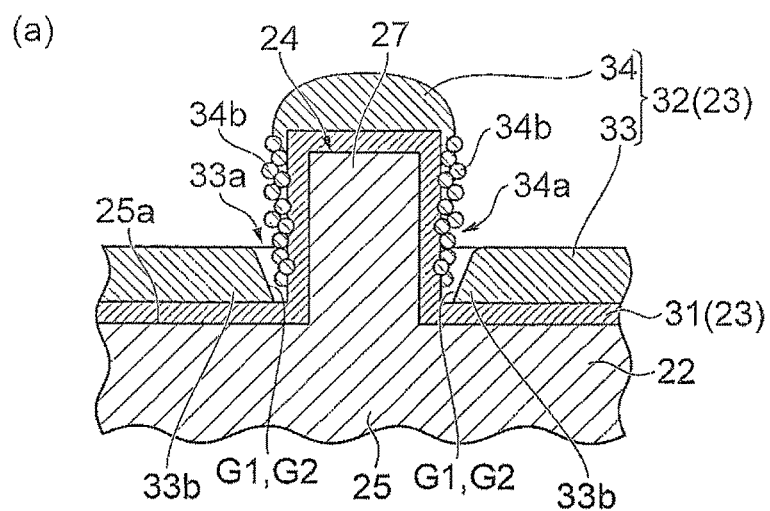
(b)
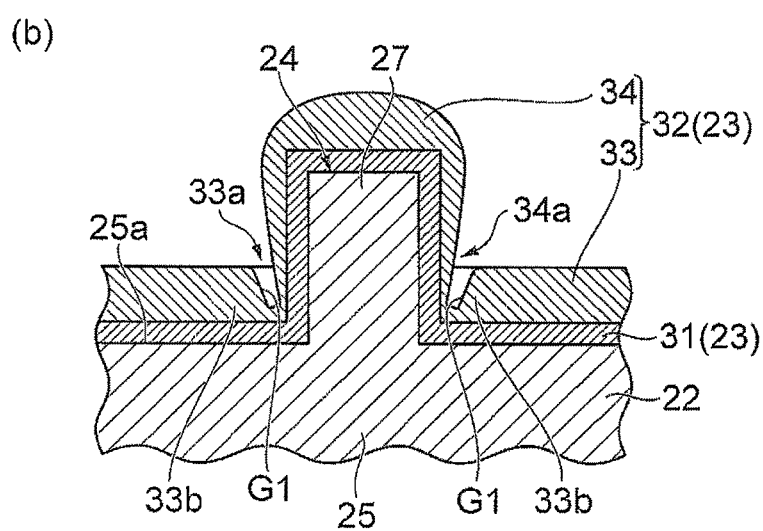
(c)
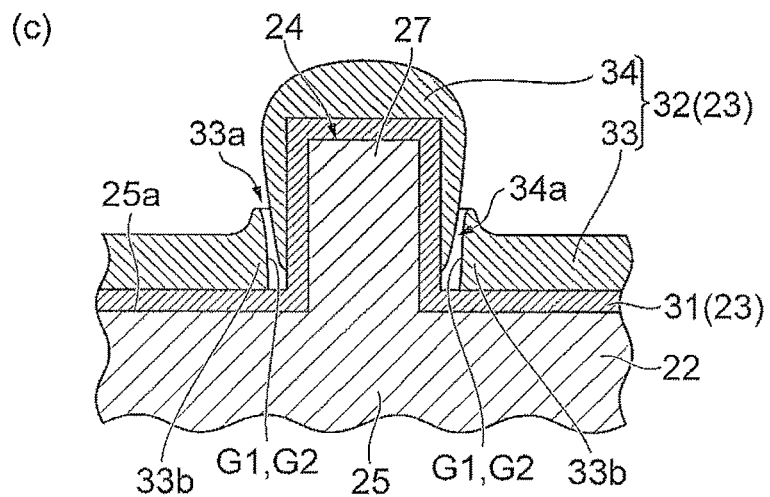

*Fig.8*
(a)
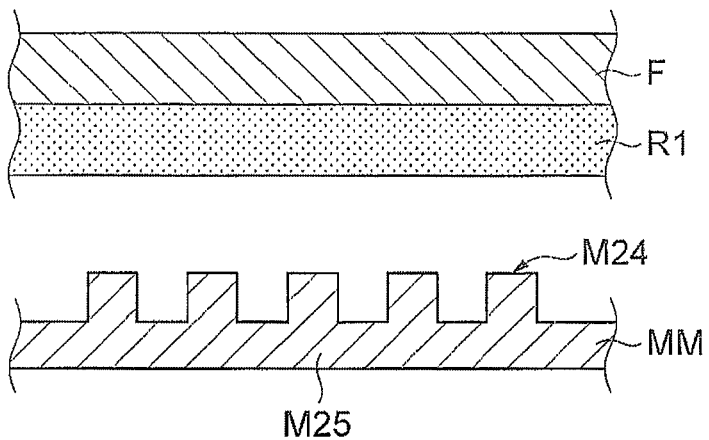
(b)
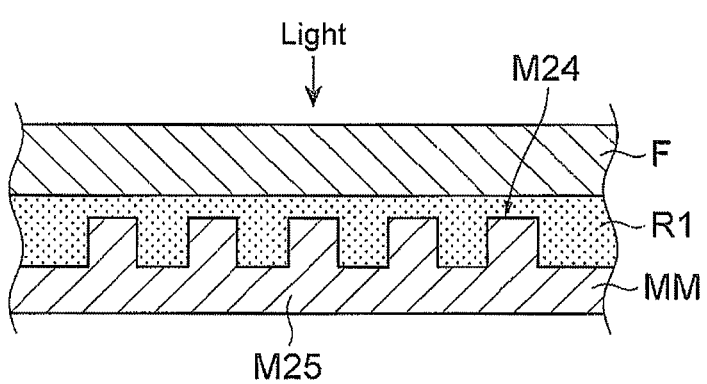
(c)
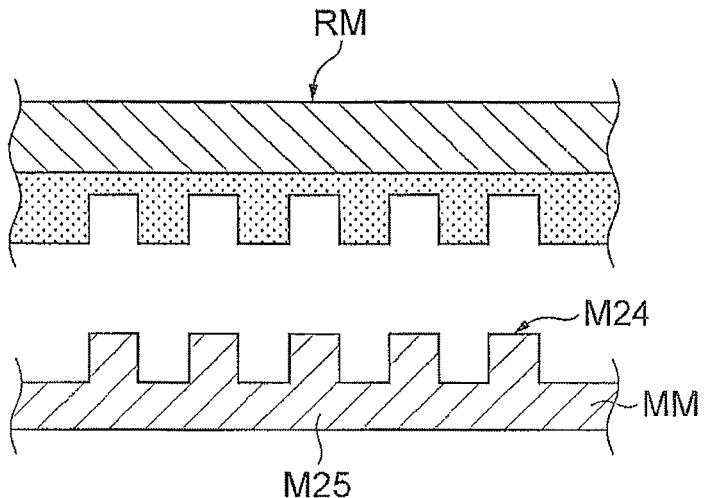

Fig.10
(a)
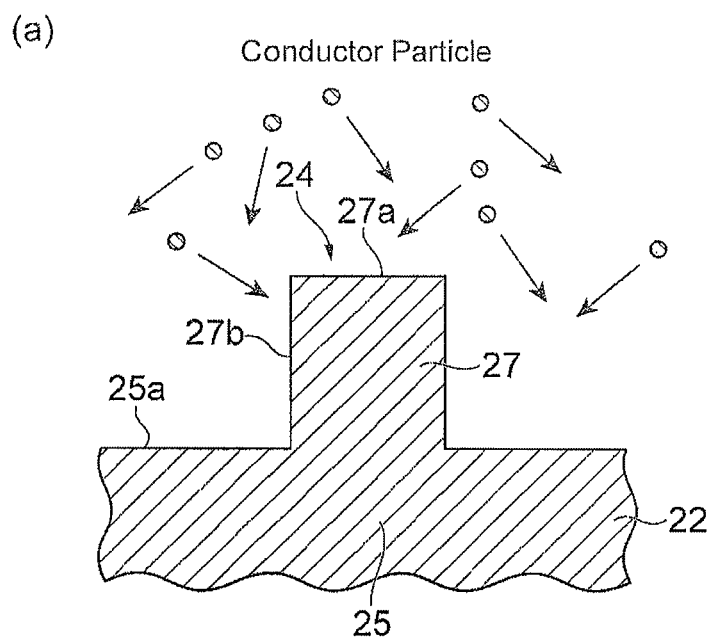
(b)
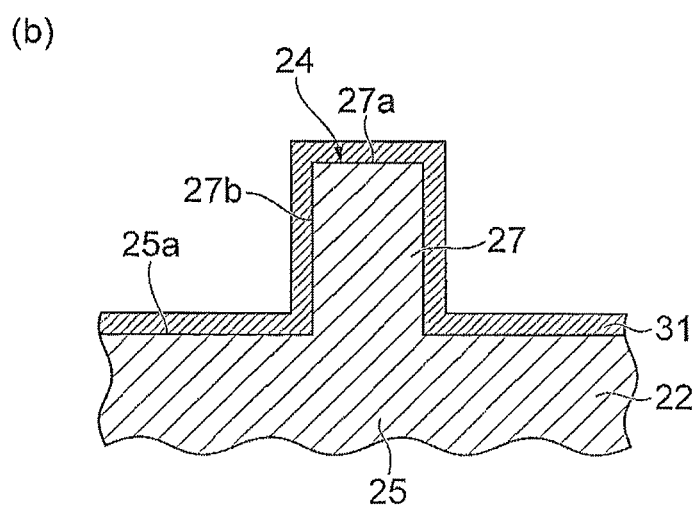

Fig. 11
(a) 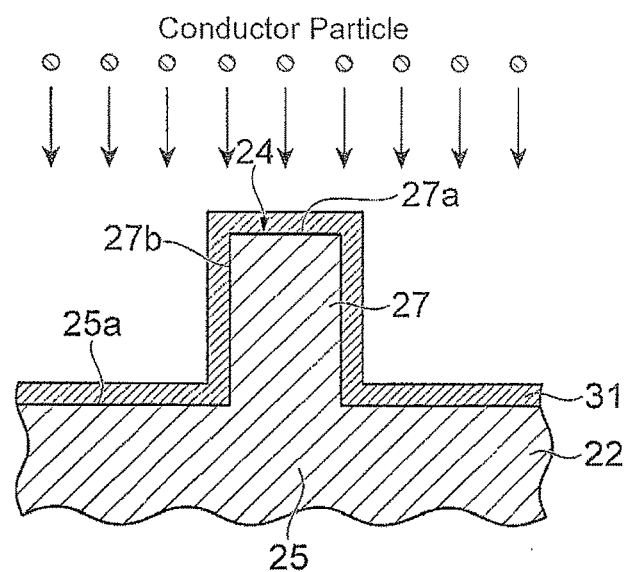
(b) 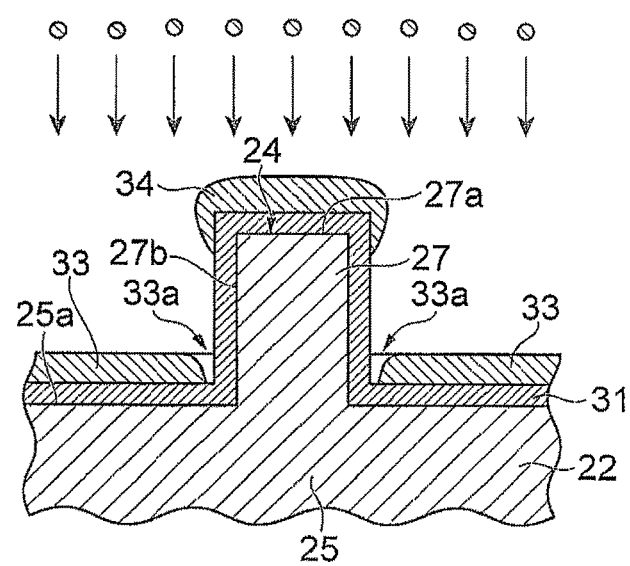
(c) 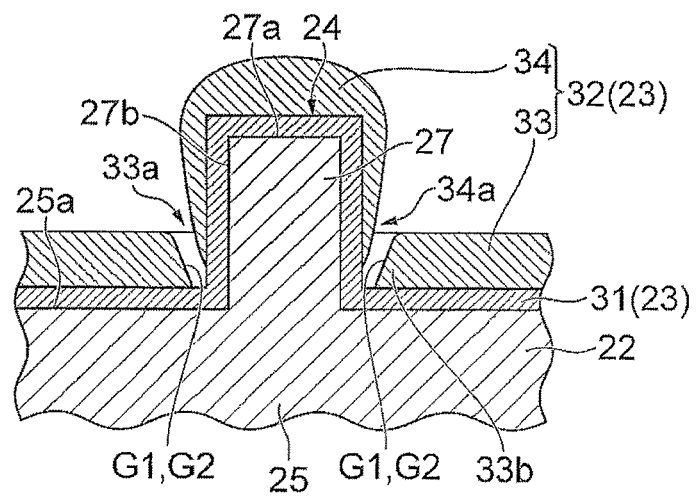

SURFACE-ENHANCED RAMAN SCATTERING ELEMENT, AND METHOD FOR MANUFACTURING SURFACE-ENHANCED RAMAN SCATTERING ELEMENT

TECHNICAL FIELD

The present invention relates to a surface-enhanced Raman scattering element and a method for manufacturing the same.

BACKGROUND ART

As a conventional surface-enhanced Raman scattering element, one equipped with a minute metal structure adapted to generate surface-enhanced Raman scattering (SERS) has been known (see, for example, Patent Literature 1 and Non Patent Literature 1). In such a surface-enhanced Raman scattering element, when a sample to be subjected to Raman spectroscopic analysis is brought into contact with the minute metal structure and is irradiated with excitation light in this state, surface-enhanced Raman scattering occurs, whereby Raman scattering light enhanced by about $10^8$ times, for example, is released.

Meanwhile, for example, Patent Literature 2 discloses a trace material detection element comprising a substrate, a plurality of minute protrusions formed on one surface of the substrate, and metal layers formed on the one surface of the substrate and upper faces of the minute protrusions. In particular in this trace material detection element, the metal layer formed on the upper faces of the minute protrusions and the metal layer formed on the one surface of the substrate are out of contact with each other, so as to form an interstice on the order of 5 nm to 10 m therebetween.

CITATION LIST

Patent Literature

Patent Literature 1: Japanese Patent Application Laid-Open No. 2011-33518
Patent Literature 2: Japanese Patent Application Laid-Open No. 2009-222507

Non Patent Literature

Non Patent Literature 1: "Q-SERS™ G1 Substrate", [online], Opto Science, Inc., [retrieved on 2013 Jul. 5]. Retrieved from the Internet: <URL: http://www.optoscience.com/maker/nanova/pdf/Q-SERS_G1.pdf>.

SUMMARY OF INVENTION

Technical Problem

When a minute metal structure is formed with a so-called nanogap as mentioned above, electric fields are locally enhanced upon irradiation with excitation light, whereby the intensity of surface-enhanced Raman scattering increases.

In the trace material detection element disclosed in Patent Literature 2, however, the side faces of the minute protrusions and a part of one surface of the substrate are exposed from the metal layers. Therefore, depending on materials constituting the minute protrusions and the substrate, contamination may occur in the metal layers under the influence of gases and the like generated from the minute protrusions and the substrate. This makes it necessary to select materials which do not generate gases and the like causing contamination in the metal layers as a material constituting the minute protrusions and the substrate. As a result, the degree of freedom in design lowers. For forming a favorable nanogap, it has also been necessary to devise the form of the minute protrusions.

It is therefore an object of one aspect of the present invention to provide a surface-enhanced Raman scattering element which can stably form a nanogap while being able to restrain the degree of freedom in design from lowering and a method for manufacturing the surface-enhanced Raman scattering element.

Solution to Problem

The surface-enhanced Raman scattering element in accordance with one aspect of the present invention comprises a substrate having a principal surface; a fine structure part, formed on the principal surface, having a plurality of projections; a first conductor layer formed on the principal surface and fine structure part so as to cover the principal surface and fine structure part continuously; and a second conductor layer formed on the first conductor layer so as to form a plurality of gaps for surface-enhanced Raman scattering; the first and second conductor layers being constituted by the same material.

In this surface-enhanced Raman scattering element, the first conductor layer is formed on the principal surface of the substrate and the fine structure part so as to cover the principal surface and fine structure part continuously. The second conductor layer is formed on the first conductor layer so as to construct a plurality of gaps for surface-enhanced Raman scattering (i.e., nanogaps contributing to increasing the intensity of surface-enhanced Raman scattering). Therefore, even if gases and the like are generated from foundation parts such as the substrate and fine structure part, the first conductor layer can reduce the influence of the gases and the like on the second conductor layer. This makes it unnecessary to restrict materials constituting the substrate, fine structure part, and the like to those which do not generate gases and the like causing contamination in the second conductor layer, whereby the degree of freedom in design can be restrained from lowering. Since the second conductor layer is formed on the first conductor layer constituted by the same material, nanogaps can also be formed stably.

In the surface-enhanced Raman scattering element in accordance with one aspect of the present invention, the second conductor layer may have a base part formed along the principal surface and a plurality of protrusions protruding from respective positions corresponding to the projections, the base part being formed with a plurality of grooves surrounding the respective protrusions when seen in the projecting direction of the projections, the gaps being formed at least within the grooves. Thus, the second conductor layer has the protrusions corresponding to the projections of the fine structure part and the base part formed with the grooves surrounding the projections. Hence, a nanogap can favorably be constructed within each groove.

In the surface-enhanced Raman scattering element in accordance with one aspect of the present invention, the gap may include at least one of a first gap formed within the groove by the base part and the protrusion and a second gap formed within the groove by the base part and the first conductor layer. Thus, within the groove, both of the first gap formed by parts of the second conductor layer and the second gap formed by the first and second conductor layers can function as nanogaps.

In the surface-enhanced Raman scattering element in accordance with one aspect of the present invention, the grooves may extend like rings so as to surround the respective projections when seen in the projecting direction of the projections. This configuration can increase gaps which favorably function as nanogaps.

In the surface-enhanced Raman scattering element in accordance with one aspect of the present invention, the protrusion may have a form constricted at an end part on the substrate side. This configuration can securely position a part of the protrusion into the groove, thereby enabling the gap formed within the groove by the base part and protrusion to function favorably as a nanogap.

In the surface-enhanced Raman scattering element in accordance with one aspect of the present invention, a part of the protrusion located within the groove corresponding thereto may be in a agglomerated state. In the surface-enhanced Raman scattering element in accordance with one aspect of the present invention, the base part may bulge along an outer edge of the groove. These configurations can enable the gap formed within the groove by the base part and protrusion to function favorably as a nanogap.

In the surface-enhanced Raman scattering element in accordance with one aspect of the present invention, the base part and the protrusion may be connected to each other at the deepest part of the groove. In the surface-enhanced Raman scattering in accordance with one aspect of the present invention, the base part and the protrusion may be separated from each other at the deepest part of the groove. These configurations can enable the gap formed within the groove by the base part and protrusion to function favorably as a nanogap.

In the surface-enhanced Raman scattering element in accordance with one aspect of the present invention, the projections may be arranged periodically along the principal surface. This configuration can stably increase the intensity of surface-enhanced Raman scattering.

The method for manufacturing a surface-enhanced Raman scattering element in accordance with one aspect of the present invention comprises a first step of forming a fine structure part having a plurality of projections on a principal surface of a substrate; a second step of forming a first conductor layer on the principal surface of the substrate and the fine structure part by a first vapor deposition method; and a third step of forming a second conductor layer for surface-enhanced Raman scattering on the first conductor layer by a second vapor deposition method; the first and second conductor layers being constituted by the same material; the second vapor deposition method having an anisotropy higher than that of the first vapor deposition method.

First, in this method, the first conductor layer is formed on the principal surface of the substrate and the fine structure part by the first vapor deposition method having a relatively low anisotropy. This causes conductor particles (atomized conductor materials) to deposit on the principal surface of the substrate and the fine structure part while having relatively random incident directions with respect to the principal surface of the substrate and the fine structure part (i.e., the conductor particles incident on the principal surface of the substrate and the fine structure part in a plurality of directions deposit on the principal surface of the substrate and the fine structure part). As a result, the first conductor layer is formed so as to cover the principal surface of the substrate and the fine structure part continuously. On the other hand, in this method, the second conductor layer is formed on the first conductor layer by the second vapor deposition method having a relatively high anisotropy. This causes conductor particles to deposit unevenly on the first conductor layer, whereby the second conductor layer is formed so as to produce a plurality of gaps (nanogaps) for surface-enhanced Raman scattering.

Therefore, even if gases and the like are generated from foundation parts such as the substrate and fine structure part, the first conductor layer can reduce the influence of the gases and the like on the second conductor layer. Hence, this method makes it unnecessary to restrict materials constituting the substrate, fine structure part, and the like to those which do not generate gases and the like causing contamination in the second conductor layer, whereby the degree of freedom in design can be restrained from lowering when manufacturing the surface-enhanced Raman scattering element. Since the second conductor layer is formed on the first conductor layer constituted by the same material, this method can form nanogaps stably.

Advantageous Effects of Invention

One aspect of the present invention can provide a surface-enhanced Raman scattering element which can stably form a nanogap while being able to restrain the degree of freedom in design from lowering and a method for manufacturing the surface-enhanced Raman scattering element.

BRIEF DESCRIPTION OF DRAWINGS

FIG. 6 is a partly enlarged sectional view of a modified example of the surface-enhanced Raman scattering element in the surface-enhanced Raman scattering unit of FIG. 1;

FIG. 8 is a sectional view illustrating steps of manufacturing the surface-enhanced Raman scattering element of FIG. 5;

FIG. 10 is a sectional view illustrating steps of manufacturing the surface-enhanced Raman scattering element of FIG. 5;

FIG. 11 is a sectional view illustrating steps of manufacturing the surface-enhanced Raman scattering element of FIG. 5;

DESCRIPTION OF EMBODIMENTS

In the following, an embodiment of one aspect of the present invention will be explained in detail with reference to the drawings. In the explanation of the drawings, the same or equivalent constituents may be referred to with the same signs while omitting their overlapping descriptions.

Figure 1:
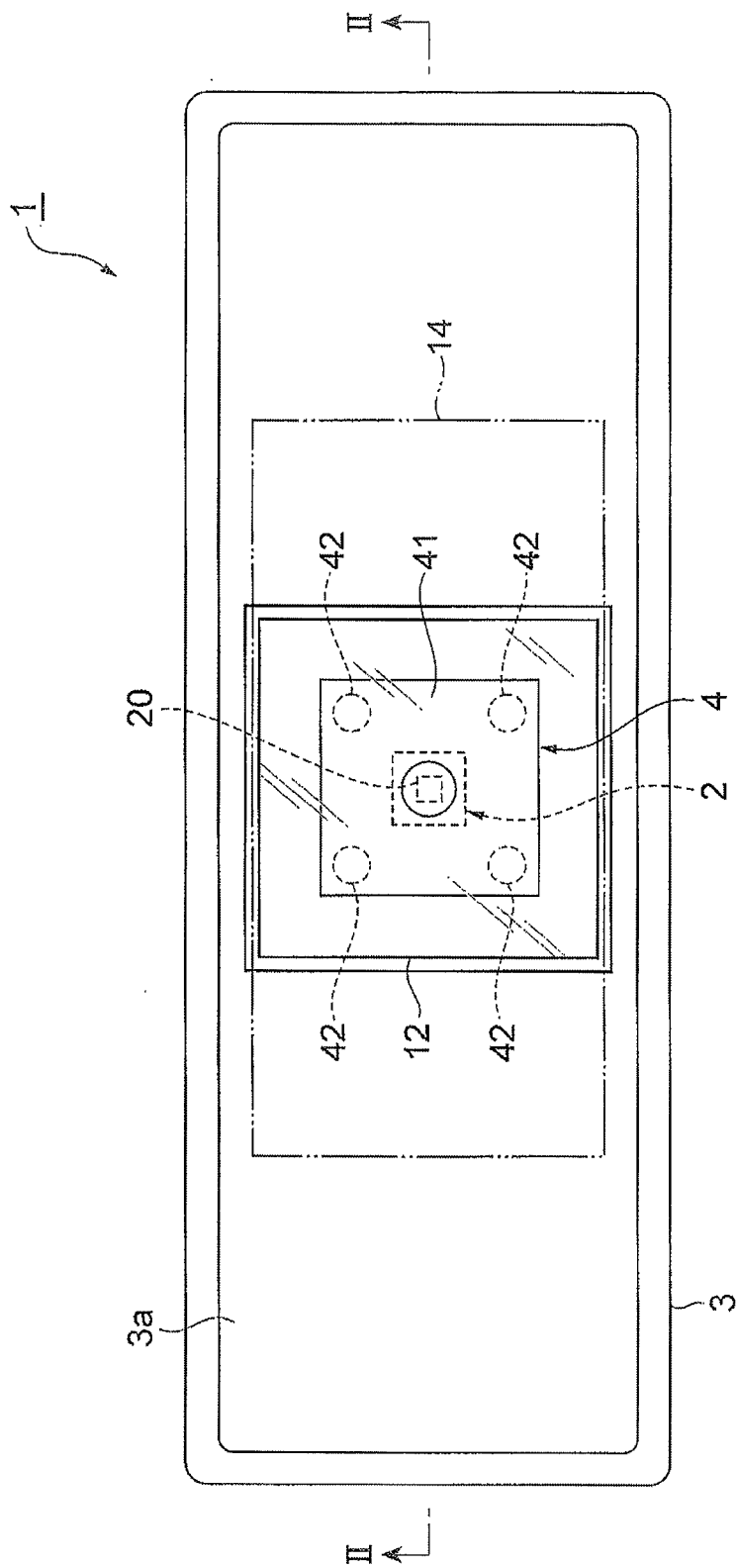
FIG. 1 is a plan view of a surface-enhanced Raman scattering unit employing a surface-enhanced Raman scattering element in accordance with an embodiment of one aspect of the present invention.
Figure 2:
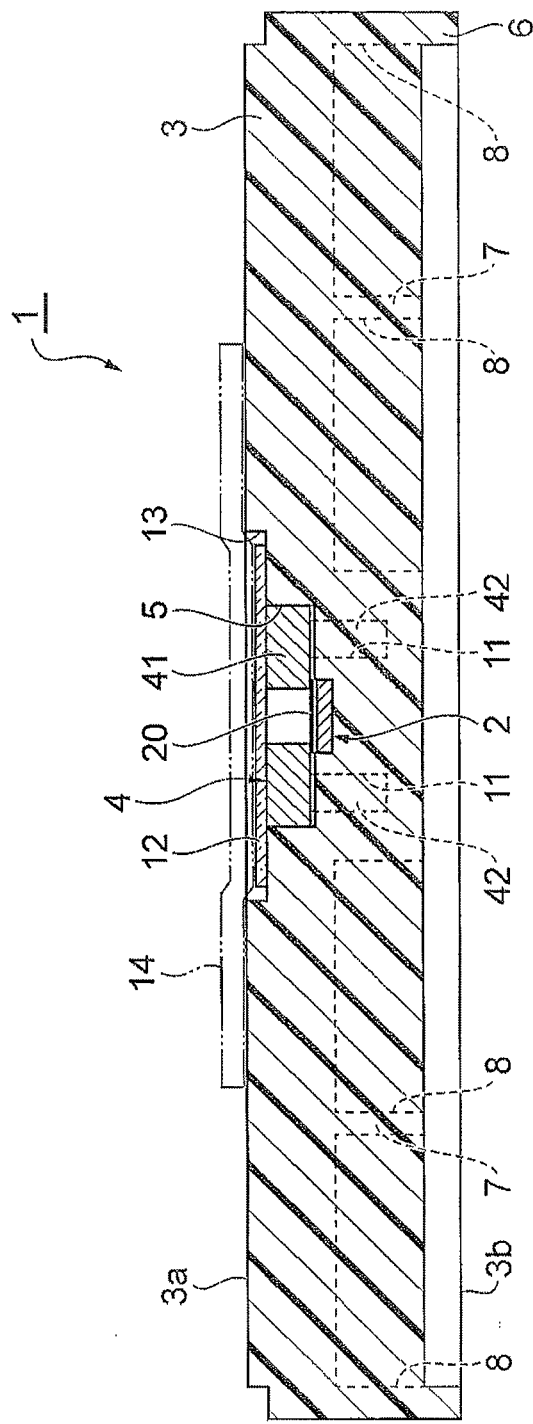
FIG. 2 is a sectional view of the surface-enhanced Raman scattering unit taken along the line II-II of FIG. 1.

As illustrated in FIGS. 1 and 2, a SERS unit (surface-enhanced Raman scattering unit) 1 comprises a SERS element (surface-enhanced Raman scattering element) 2, a measurement board 3 supporting the SERS element 2 at the time of measurement, and a holding part 4 mechanically holding the SERS element 2 in the measurement board 3. By "mechanically" is meant "by fitting between members without adhesives and the like."

Figure 3:
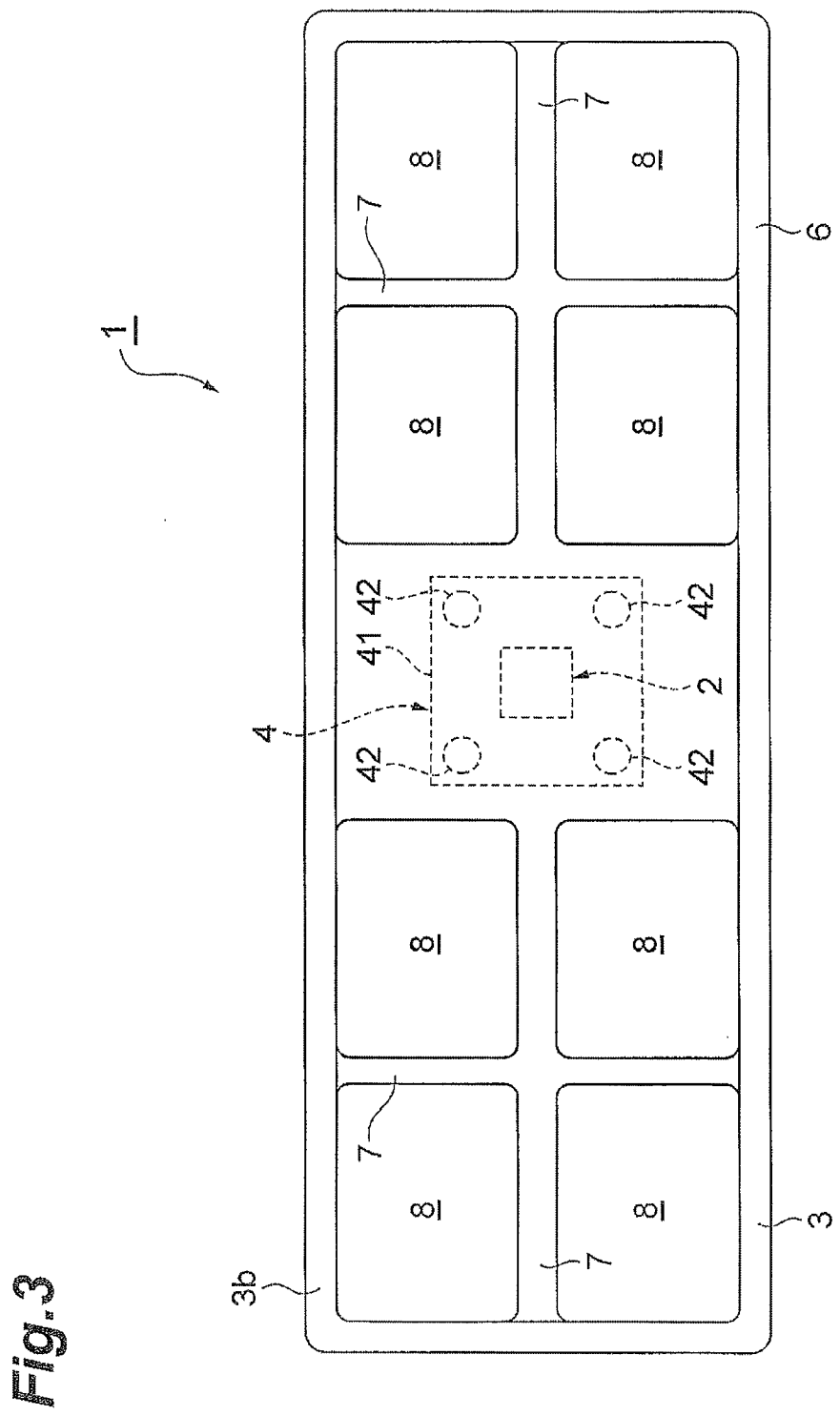
FIG. 3 is a bottom view of the surface-enhanced Raman scattering unit of FIG. 1.

The measurement board 3 has a front face 3a provided with a depression 5 containing the SERS element 2 and holding part 4. On the other hand, as illustrated in FIGS. 2 and 3, the measurement board 3 has a rear face 3b provided with a plurality of hollowed parts 8 so as to form wall parts 6, 7 extending in directions perpendicular to the thickness direction of the measurement board 3. By way of example, the wall part 6 is formed like a ring along the outer edge of the measurement board 3, while the wall parts 7 are formed like a grid on the inside of the wall part 6. The measurement board 3 is formed into a rectangular plate. The depression 5 and hollowed parts 8 are formed into rectangular parallelepipeds. The measurement board 3 like this is integrally formed from a material such as a resin (examples of which include polypropyrene, styrol resin, ABS resin, polyethylene, PET, PMMA, silicone, and liquid crystal polymers), ceramics, glass, or silicon by using a technique such as molding, cutting, or etching.

Figure 4:
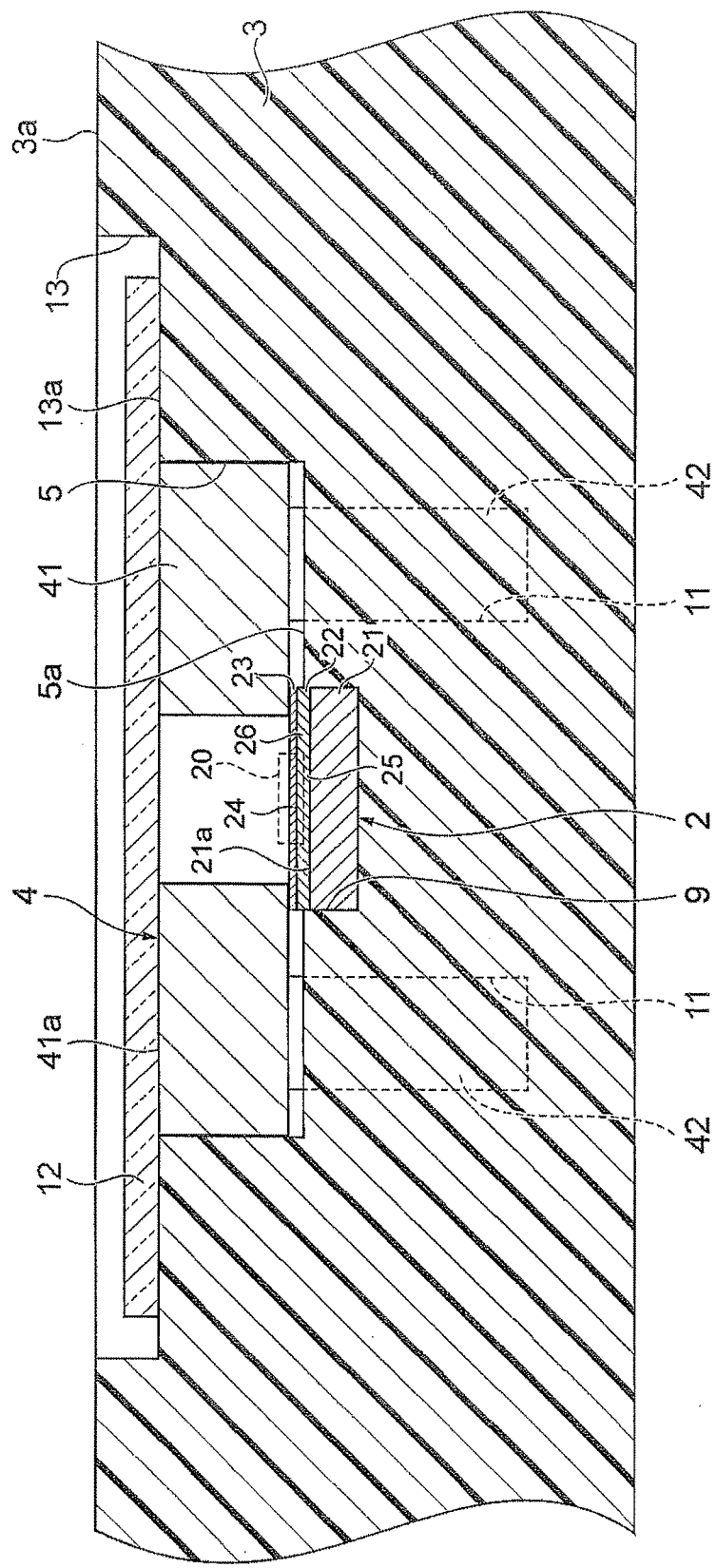
FIG. 4 is a partly enlarged sectional view of the surface-enhanced Raman scattering unit taken along the line II-II of FIG. 1.

As illustrated in FIG. 4, the SERS element 2 comprises a substrate 21, a molded layer 22 formed on the substrate 21, and a conductor layer 23 formed on the molded layer 22. By way of example, the substrate 21 is formed into a rectangular plate by silicon, glass, or the like and has an outer form on the order of several hundred μm×several hundred μm to several ten mm×several ten mm and a thickness on the order of 100 μm to 2 mm.

The molded layer 22 includes a fine structure part 24, a support part 25, and a frame part 26. The fine structure part 24, which is a region having a periodic pattern constructed on a surface layer on the side opposite from the substrate 21 at a center part of the molded layer 22, is formed on a front face (principal surface) 21a of the substrate 21 with the support part 25 interposed therebetween. The support part 25, which is a region supporting the fine structure part 24, is formed on the front face 21a of the substrate 21. The frame part 26, which is a ring-shaped region surrounding the support part 25, is formed on the front face 21a of the substrate 21.

By way of example, the fine structure part 24 has a rectangular outer form on the order of several hundred μm×several hundred μm to several ten mm×several ten mm when seen from one side in the thickness direction of the measurement board 3. As a periodic pattern, a plurality of pillars, each having a width and height on the order of several nm to several hundred nm, are periodically arranged in the fine structure part 24 at a pitch on the order of several ten nm to several hundred nm along the front face 21a of the substrate 21. The support part 25 and frame part 26 have a thickness on the order of several ten nm to several ten μm. The molded layer 22 like this is integrally formed by molding a resin (examples of which include resins based on acrylics, fluorine, epoxy, silicone, and urethane, PET, polycarbonate, and inorganic/organic hybrid materials) or low-melting glass arranged on the substrate 21 by nanoimprinting, for example.

The conductor layer 23 is integrally formed on the fine structure part 24 and frame part 26. In the fine structure part 24, the conductor layer 23 reaches a surface of the support part 25 which is exposed to the side opposite from the substrate 21. In the SERS element 2, the conductor layer 23 formed on the surface of the fine structure part 24 and on the surface of the support part 25 exposed to the side opposite from the substrate 21 constructs an optical function part 20 which generates surface-enhanced Raman scattering. By way of example, the conductor layer 23 has a thickness on the order of several nm to several μm. The conductor layer 23 like this is formed by vapor-depositing a conductor such as a metal (Au, Ag, Al, Cu, Pt, or the like) on the molded layer 22 molded by nanoimprinting, for example.

The depression 5 has a bottom face 5a provided with a recess 9 which contains a part on the substrate 21 side of the SERS element 2. The recess 9 is formed complementary to a part on the substrate 21 side of the SERS element 2 and restrains the SERS element 2 from moving in directions perpendicular to the thickness direction of the substrate 21. The SERS element 2 is merely in contact with the inner surface of the recess 9 without being secured thereto with adhesives and the like. The recess 9 may contain substantially the whole SERS element 2 so that the front face (surface on the side opposite from the substrate 21) of the conductor layer 23 and the bottom face 5a of the depression 5 are substantially flush with each other.

The holding part 4 has a constraining part 41 formed like a ring so as to surround the optical function part 20 when seen in the thickness direction of the substrate 21 and a plurality of legs 42 extending from the constraining part 41 to the rear face 3b side of the measurement board 3. The bottom face 5a of the depression 5 is formed with fitting holes 11 corresponding to the respective legs 42. The legs 42 are fitted into the respective fitting holes 11 while the constraining part 41 surrounds the optical function part 20 and is in contact with the conductor layer 23 of the SERS element 2. Thus, the holding part 4 formed separately from the measurement board 3 is mechanically secured to the measurement board 3, while the SERS element 2 arranged in the recess 9 is held between the measurement board 3 and the constraining part 41 of the holding part 4. As a consequence, the SERS element 2 is mechanically held against the measurement board 3. The fitting holes 11 have bottoms and do not penetrate through the measurement board 3.

By way of example, the constraining part 41 is formed such as to have a rectangular outer edge and a circular inner edge when seen in the thickness direction of the substrate 21, while the legs 42 extend respectively from four corners of the constraining part 41 to the rear face 3b side of the measurement board 3. The constraining part 41 has the circular inner edge, thereby keeping pressures from locally acting on the SERS element 2. The legs 42 and fitting holes 11 are formed cylindrical. The holding part 4 having the constraining part 41 and legs 42 like these is integrally formed from a material such as a resin (examples of which include polypropyrene, styrol resin, ABS resin, polyethylene, PET, PMMA, silicone, and liquid crystal polymers), ceramics, glass, or silicon by using a technique such as molding, cutting, or etching.

The SERS unit 1 further comprises a light-transmitting cover 12. The cover 12 is arranged in a widened part 13 provided in the opening of the depression 5 and covers the opening of the depression 5. The widened part 13 is formed complementary to the cover 12 and restrains the cover 12 from moving in directions perpendicular to the thickness direction of the cover 12. The constraining part 41 of the holding part 4 has a surface 41a substantially flush with a bottom face 13a of the widened part 13. As a consequence, the cover 12 is supported not only by the measurement board 3 but also by the holding part 4. By way of example, the cover 12 is formed into a rectangular plate by glass or the like and has an outer form on the order of 18 mm×18 mm and a thickness of about 0.15 mm. As illustrated in FIGS. 1 and 2, a temporary securing film 14 is attached to the measurement board 3 before using the SERS unit 1 so as to shield the cover 12, thereby preventing the cover 12 from dropping out of the measurement board 3.

Figure 5:
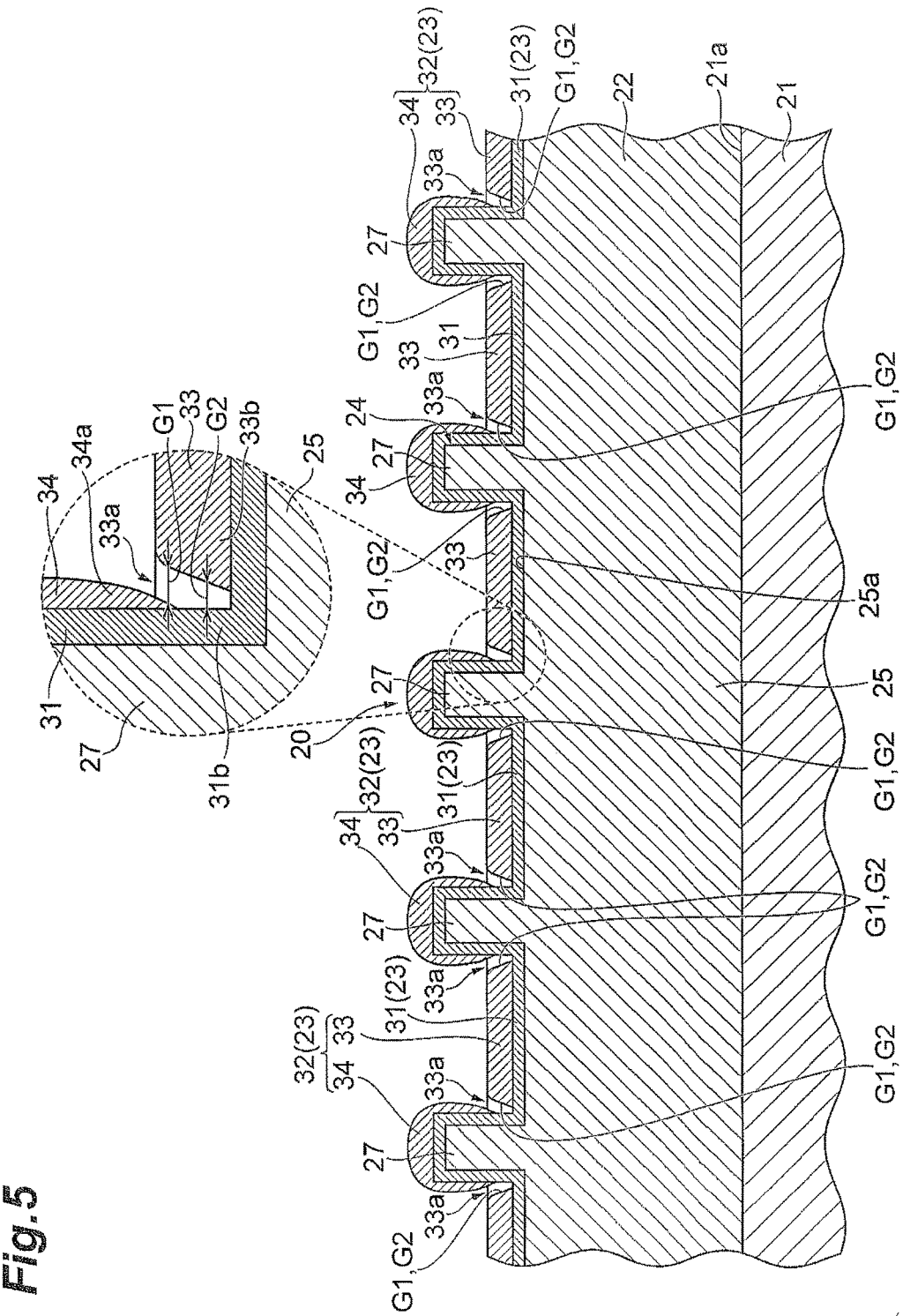
FIG. 5 is a partly enlarged sectional view of the surface-enhanced Raman scattering element in the surface-enhanced Raman scattering unit of FIG. 1.

The above-mentioned SERS element 2 will be explained in more detail. As illustrated in FIG. 5, the fine structure part 24 has a plurality of pillars (projections) 27 periodically arranged along the front face 21a of the substrate 21. By way of example, the pillars 27, each of which is formed into a circular column having a diameter and height on the order of several nm to several hundred nm, are periodically arranged at a pitch on the order of several ten nm to several hundred nm (preferably 250 nm to 800 nm) along the front face 21a of the substrate 21.

The conductor layer 23 has a first conductor layer 31 and a second conductor layer 32. The first and second conductor layers 31, 32 are sequentially stacked on the molded layer 22. The first conductor layer 31 is formed all over the front face 21a of the substrate 21 and the fine structure part 24 (molded layer 22) so as to cover them continuously. The first conductor layer 31 is constituted by a conductor material such as Au, Ag, Al, Cu, or Pt, for example. The first conductor layer 31 has a thickness on the order of several nm to several hundred nm, for example.

The second conductor layer 32 is formed on the first conductor layer 31 so as to construct a plurality of gaps for surface-enhanced Raman scattering (i.e., nanogaps contributing to increasing the intensity of surface-enhanced Raman scattering). More specifically, the second conductor layer 32 has a base part 33 formed along the front face 21a of the substrate 21 and a plurality of protrusions 34 protruding from the base part 33 at respective positions corresponding to the pillars 27.

The base part 33 is formed like a layer on a surface 25a of the support part 25 with the first conductor layer 31 interposed therebetween. The base part 33 has a thickness on the order of several nm to several μm, for example. Therefore, the total thickness of the first conductor layer 31 and base part 33, an example of which is on the order of several nm to several μm, is smaller than the height of the pillars 27. Each protrusion 34 is produced so as to cover its corresponding pillar 27 and has a form constricted at least at an end part 34a on the substrate 21 side. In each protrusion 34, at least an end part on the side opposite from the substrate 21 (a part located on the top part of the pillar 27) protrudes from the base part 33.

The base part 33 is formed with a plurality of grooves 33a opening to the side opposite from the substrate 21. The grooves 33a extend like circular rings so as to surround the respective pillars 27 when seen in the projecting direction of the pillars 27 (i.e., the thickness direction of the substrate 21). The end part 34a of each protrusion 34 is located within its corresponding groove 33a (i.e., within the groove 33a surrounding the pillar 27 formed with this protrusion 34). As a consequence, within each groove 33a, the base part 33 and protrusion 34 form a first gap G1 opening to the side opposite from the substrate 21. The first gap G1 is a fine interstice formed between an edge part 33b of the base part 33 forming the groove 33a therein and the end part 34a of the protrusion 34 (i.e., between parts made of a conductor material).

On the other hand, the end part 34a of each protrusion 34 does not reach the deepest part of its corresponding groove 33a. That is, the base part 33 and protrusion 34 are separated from each other at the deepest part of each groove 33a. Therefore, the first conductor layer 31 is covered with the protrusion 34 near the opening of each groove 33a but exposed from the protrusion 34 near the deepest part of each groove 33a. As a consequence, within each groove 33a, the base part 33 and first conductor layer 31 form a second gap G2. The second gap G2 is a fine interstice formed between the edge part 33b of the base part 33 forming the groove 33a therein and a part 31b of the first conductor layer 31 formed on the side face of a root part of the pillar 27 (i.e., between parts made of a conductor material).

By way of example, the first and second gaps G1, G2 extend like circular rings surrounding their corresponding pillars 27 and have a width on the order of 0 to several ten nm when seen in the projecting direction of the pillars 27. That is, each of the first and second gaps G1, G2 functions as a nanogap contributing to increasing the intensity of surface-enhanced Raman scattering. While the outer side face defining the groove 33a is formed by the base part 33, the inner side face defining the groove 33a may be formed by either the base part 33 or the first conductor layer 31. The bottom face defining the groove 33a may be formed by either the base part 33 or the first conductor layer 31.

The second conductor layer 32 like this may be formed on the first conductor layer 31 so as to extend all over the front face 21a of the substrate 21 (i.e., all over the molded layer 22) or only on the region formed with the fine structure part 24. The second conductor layer 32 is made of the same material as with the first conductor layer 31, examples of which include conductor materials such as Au, Ag, Al, Cu, and Pt.

Here, the first conductor layer 31 is formed by a vapor deposition method having a relatively low anisotropy, such as sputtering or ion plating, from the above-mentioned conductor materials, for example. On the other hand, the second conductor layer 32 is formed by a vapor deposition method having a relatively large anisotropy, such as evaporation method, for example, from the same material as with the first conductor layer. Therefore, the first conductor layer 31 is formed as conductor particles (atomized conductor materials) having relatively random incident directions with respect to the fine structure part 24 (molded layer 22) deposit on the fine structure part 24 (i.e., formed as the conductor particles incident on the fine structure part 24 in a plurality of directions deposit on the fine structure part 24). Hence, the first conductor layer 31 is continuously formed all over the front face 21a of the substrate 21 relatively uniformly. On the other hand, the second conductor layer 32 is formed as conductor particles having a substantially fixed incident direction with respect to the first conductor layer 31 deposit on the first conductor layer 31, for example. As a consequence, there are parts (e.g., grooves 33a) where the second conductor layer 32 is not formed on the front face 21a of the substrate 21.

As illustrated in (a) of FIG. 6, there is a case where a plurality of agglomerates (particles) 34b constructed by agglomerated conductor particles are formed in the protrusion 34 of the second conductor layer 32 (i.e., in the state of agglomerated conductor particles). While (a) of FIG. 6 illustrates a case where a part of the protrusion 34 which corresponds to the side face of the pillar 27 is in the agglomerated state, only the end part 34a located within its corresponding groove 33a may be in the agglomerated state. Thus forming the protrusion 34 with a plurality of agglomerates 34b may produce gaps functioning as nanogaps between the agglomerates 34b in addition to the gaps (first gaps G1) between the base part 33 and agglomerates 34b.

As illustrated in (b) of FIG. 6, there is a case where the base part 33 and protrusion 34 are connected to each other at the deepest part of the groove 33a. In this case, the first conductor layer 31 is not exposed within the groove 33a, whereby the first gap G1 is formed alone without the above-mentioned second gap G2. As illustrated in (c) of FIG. 6, there is a case where the base part 33 and protrusion 34 are separated from each other at the deepest part of the groove 33a while the base part 33 (the edge part 33b in particular) bulges along the outer edge of the groove 33a. Further, there is a case where the base part 33 and protrusion 34 are connected to each other at the deepest part of the groove 33a while the base part 33 (the edge part 33b in particular) bulges along the outer edge of the groove 33a.

Figure 7:
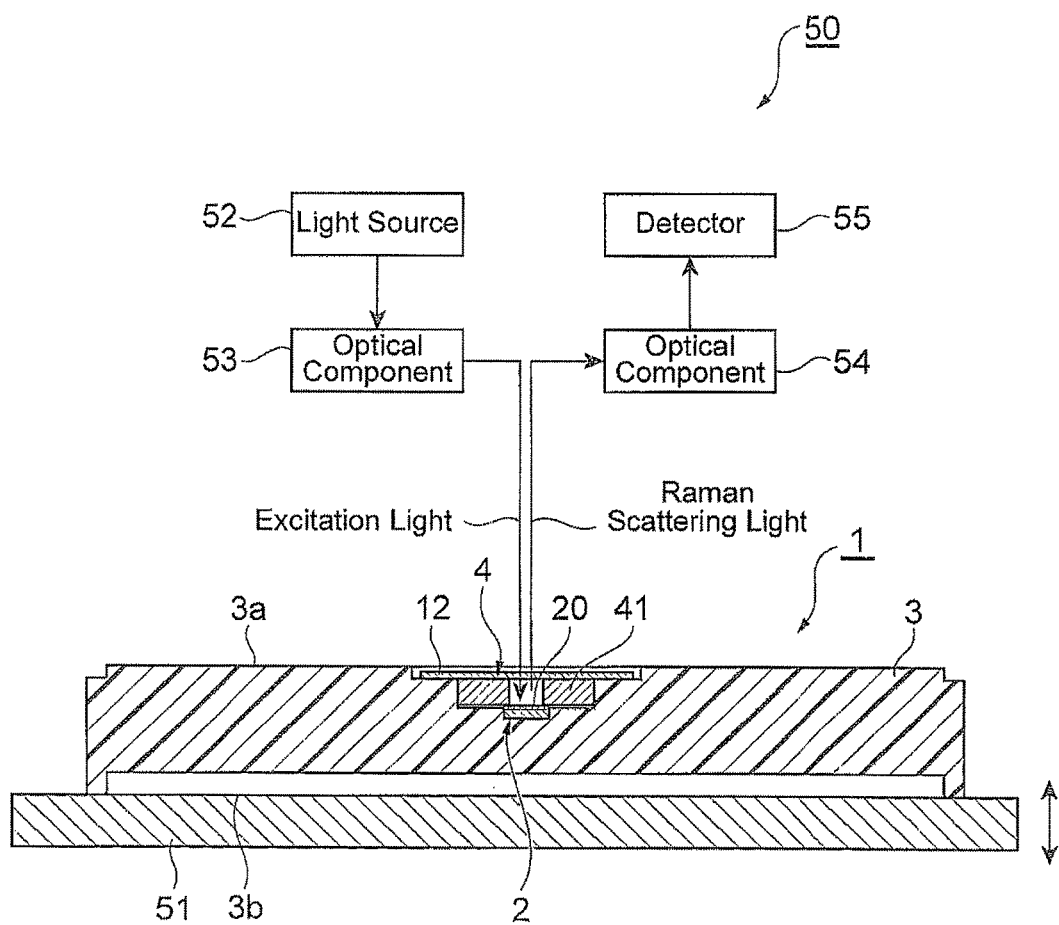
FIG. 7 is a diagram of a Raman spectroscopic analyzer in which the surface-enhanced Raman scattering unit of FIG. 1 is set.

A Raman spectroscopic analysis method by the SERS unit 1 constructed as in the foregoing will now be explained. Here, as illustrated in FIG. 7, the Raman spectroscopic analysis method is performed in a Raman spectroscopic analyzer 50 comprising a stage 51 for supporting the SERS unit 1, a light source 52 for emitting excitation light, an optical component 53 for carrying out collimation, filtering, condensing, and the like necessary for irradiating the optical function part 20 with the excitation light, an optical component 54 for carrying out collimation, filtering, and the like necessary for guiding Raman scattering light to a detector 55, and the detector 55 for detecting the Raman scattering light.

First, the SERS unit 1 is prepared, the temporary securing film 14 is peeled from the measurement board 3, and the cover 12 is removed from the measurement board 3. Then, a solution sample (or a dispersion of a powder sample in a solution such as water or ethanol) is dropped to a region on the inside of the constraining part 41 of the holding part 4, so as to arrange the solution sample on the optical function part 20. Subsequently, for reducing the lens effect, the cover 12 is arranged on the widened part 13 of the measurement board 3 and brought into close contact with the solution sample.

Thereafter, the measurement board 3 is arranged on the stage 51, and the SERS unit 1 is set in the Raman spectroscopic analyzer 50. Subsequently, the solution sample arranged on the optical function part 20 is irradiated with the excitation light emitted from the light source 52 through the optical component 53, so as to excite the solution sample. At this time, the stage 51 is moved such that the excitation light has a focal point located at the optical function part 20. This generates surface-enhanced Raman scattering at the interface between the optical function part 20 and solution sample, whereby surface-enhanced Raman scattering light derived from the solution sample is enhanced by about $10^8$ times, for example, and released. The released Raman scattering light is detected by the detector 55 through the optical component 54, whereby Raman spectroscopic analysis is performed.

Not only the above-mentioned method, but the following methods may also be used for arranging the sample on the optical function part 20. For example, while holding the measurement board 3, the SERS element 2 may be dipped in and lifted from the solution sample (or a dispersion of a powder sample in a solution such as water or ethanol), and then the sample may be blown to dry. A minute amount of the solution sample (or a dispersion of a powder sample in a solution such as water or ethanol) may be dropped onto the optical function part 20 and left to dry. A powder sample may be dispersed as it is on the optical function part 20. In these modes, it is not necessary for the cover 12 to be arranged at the time of measurement.

In the SERS element 2, as explained in the foregoing, the first conductor layer 31 is formed on the front face 21a of the substrate 21 and the fine structure part 24 so as to cover the front face 21a and fine structure part 24 continuously. The second conductor layer 32 is formed on the first conductor layer 31 so as to produce gaps (e.g., the first and second gaps G1, G2) functioning as nanogaps. Therefore, even if gases and the like are generated from foundation parts such as the substrate 21 and fine structure part 24, the first conductor layer 31 can reduce the influence of the gases and the like on the second conductor layer 32. This makes it unnecessary to restrict materials constituting the substrate 21, fine structure part 24, and the like to those which do not generate gases and the like causing contamination in the second conductor layer, whereby the degree of freedom in design can be restrained from lowering. Since the second conductor layer 32 is formed on the first conductor layer 31 constituted by the same material, nanogaps can also be formed stably.

In the SERS element 2, the second conductor layer has the protrusions 34 corresponding to the pillars 27 of the fine structure part 24 and the base part 33 having the grooves 33a formed so as to surround the pillars 27. Therefore, a nanogap can favorably be constructed within each groove 33a.

In the SERS element 2, the pillars 27 are periodically arranged along the front face 21a of the substrate 21. This can increase the intensity of surface-enhanced Raman scattering.

In the SERS element 2, the grooves 33a extend like rings so as to surround the pillars 27 when seen in the projecting direction of the pillars 27. This can increase gaps (first and second gaps G1, G2) which favorably function as nanogaps.

In the SERS element 2, the protrusion 34 has a form constricted at an end part 34a on the substrate 21 side. This can securely position the end part 34a of the protrusion 34 into the groove 33a formed in the base part 33, thereby enabling the first gap G1 formed within the groove 33a by the base part 33 and protrusion 34 to function favorably as a nanogap.

In the SERS element 2, the first gap G1 formed within the groove 33a by the base part 33 and protrusion 34 can favorably function as a nanogap either when the end part 34a of the protrusion 34 located within the groove 33a is in the agglomerated state or the base part 33 bulges along the outer edge of the groove 33a.

In the SERS element 2, the base part 33 and protrusion 34 are separated from each other at the deepest part of the groove 33a. Therefore, not only the first gap G1 formed by the base part 33 and protrusion 34, but the second gap G2 formed by the base part 33 and first conductor layer 31 can also favorably function as a nanogap.

In the SERS element 2, the base part 33 and protrusion 34 may be separated from each other at the deepest part of the groove 33a, which can also enable the first gap G1 formed by the base part 33 and protrusion 34 to function favorably as a nanogap.

An example of methods for manufacturing the SERS element 2 will now be explained. First, as illustrated in (a) of FIG. 8, a film base F is prepared, and a UV-curable resin is applied to a surface of the film base F, so as to form a UV-curable resin layer R1 on the film base F. On the other hand, a master mold MM is prepared. The master mold MM includes a fine structure part M24 corresponding to the fine structure part 24 and a support part M25 supporting the fine structure part M24. The upper side of the master mold MM is surface-treated with a releasing agent or the like so as to be released easily at a later step.

Next, as illustrated in (b) of FIG. 8, the master mold MM is pressed against the UV-curable resin layer R1 on the film base F, and the UV-curable resin R1 is irradiated with UV in this state, so as to be cured, whereby a pattern of the plurality of fine structure parts M24 is transferred to the UV-curable resin R1. Then, as illustrated in (c) of FIG. 8, the master mold MM is released from the UV-curable resin R1 on the film base F, so as to yield a replica mold (replica film) RM having the pattern of the plurality of fine structure parts M24 transferred thereto. The replica mold RM may be surface-treated with a releasing agent or the like so as to be released easily at a later step.

Subsequently, as illustrated in (a) of FIG. 9, a silicon wafer W to become the substrate 21 is prepared, and a UV-curable resin is applied to a surface of the silicon wafer W, so as to form a nanoimprinting layer R2 to become the molded layer 22 on the silicon wafer W. Then, as illustrated in (b) of FIG. 9, the replica mold RM is pressed against the nanoimprinting layer R2 on the silicon wafer W, and the nanoimprinting layer R2 is irradiated with UV in this state, so as to be cured, whereby a pattern of the replica mold RM is transferred to the nanoimprinting layer R2.

Figure 9:
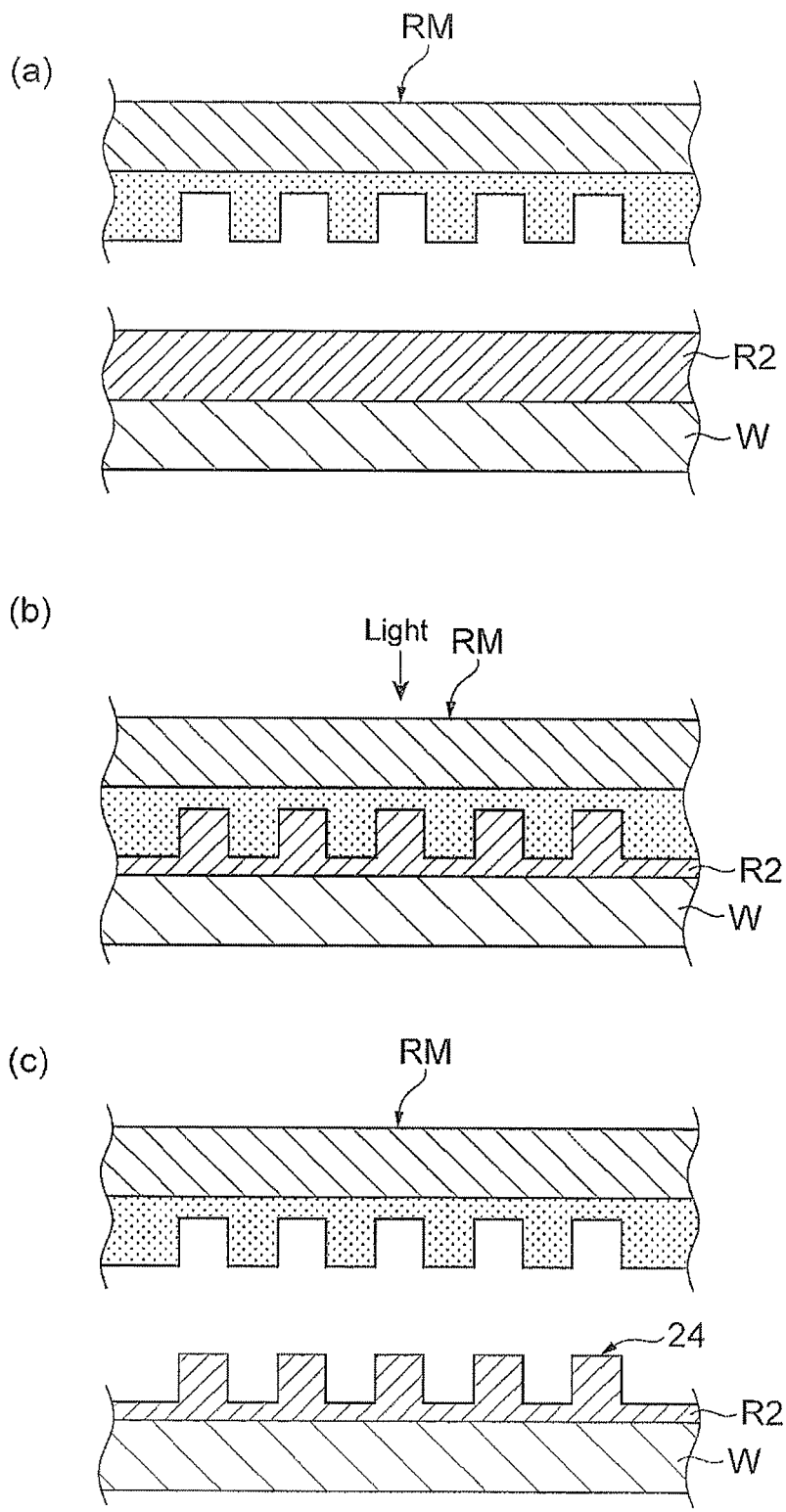
FIG. 9 is a sectional view illustrating steps of manufacturing the surface-enhanced Raman scattering element of FIG. 5.

Thereafter, as illustrated in (c) of FIG. 9, the replica mold RM is released from the nanoimprinting layer R2 on the silicon wafer W, so as to yield the silicon wafer W formed with a plurality of fine structure parts 24 (molded layer 22). That is, the fine structure parts 24 having a plurality of pillars 27 are formed on the front face 21a of the substrate 21 in this step (first step).

Next, a metal such as Au or Ag (the above-mentioned conductor material) is deposited on the front face 21a of the substrate 21 and the fine structure parts 24 (molded layer 22), so as to form the first and second conductor layers 31, 32. Here, as illustrated in FIG. 10, the conductor material is initially deposited on the front face 21a of the substrate 21 and the fine structure parts 24 by the first vapor deposition method having a relatively low anisotropy such as sputtering or ion plating, so as to form the first conductor layer 31 on the front face 21a of the substrate 21 and the fine structure parts 24 (second step).

Since this step uses the first vapor deposition method having a relatively low anisotropy, as illustrated in (a) of FIG. 10, conductor particles having relatively random incident directions with respect to the fine structure parts 24 (molded layer 22) deposit on the fine structure parts 24 (molded layer 22) (i.e., the conductor particles incident on the fine structure parts 24 in a plurality of directions deposit on the fine structure parts 24), thereby forming the first conductor layer 31. Hence, the first conductor layer 31 is formed on the front face 21a of the substrate 21 and the fine structure parts 24 so as to continuously cover the whole front face 21a. The first conductor layer 31 is formed so as to have a substantially uniform thickness on top parts 27a of the pillars 27, side faces 27b of the pillars 27, and the surface 25a of the support part 25.

Next, as illustrated in FIG. 11, the same conductor material as that of the first conductor layer 31 is deposited on the first conductor layer 31 by the second vapor deposition method having a relatively high anisotropy such as evaporation method (examples of which include resistance heating vacuum vapor deposition, electron beam heating vacuum vapor deposition, and high-frequency heating vacuum vapor deposition), so as to form the second conductor layer 32 on the first conductor layer 31 (third step). The anisotropy of the second vapor deposition method is higher than that of the first vapor deposition method for forming the first conductor layer 31.

Since this step uses the second vapor deposition method having a relatively high anisotropy (e.g., performs evaporation method in a state where the relative positional relationship between a evaporation source and the first conductor layer 31 (fine structure parts 24) is fixed within a vapor deposition system), conductor particles having a substantially fixed incident direction with respect to the first conductor layer 31 deposit on the first conductor layer 31, thereby forming the second conductor layer 32. By the conductor particles having a substantially fixed incident direction with respect to the first conductor layer 31 is meant to encompass a case where most of the conductor particles are incident on the first conductor layer 31 in a predetermined direction while a small number of the conductor particles are incident on the first conductor layer 31 in directions different from the predetermined direction. Hence, there are parts such as the above-mentioned grooves 33a where the second conductor layer 32 is not formed on the front face 21a of the substrate 21. More specifically, when the conductor particles are deposited on the first conductor layer 31 in the projecting direction of the pillar 27 as illustrated in (a) of FIG. 11, the conductor particles are easy to reach (easy to adhere to) parts on the surface 25a of the support part 25 and the top part 27a of the pillar 27 in the first conductor layer 31 as illustrated in (b) of FIG. 11.

On the other hand, the conductor particles are hard to reach (hard to adhere to) parts of the first conductor layer 31 near the root of the pillar 27 under a shadow effect of the conductor layer (protrusion 34) deposited on the top part 27a of the pillar 27. As a consequence, the groove 33a is formed in the base part 33 so as to surround the pillar 27. The conductor particles are also hard to adhere to parts of the first conductor layer 31 on the side face 27b of the pillar 27 under a similar shadow effect. This causes the protrusion 34 to have a form constricted at the end part 34a, thereby positioning the end part 34a of the protrusion 34 into the groove 33a.

Thus forming the first conductor layer 31 on the fine structure part 24, and the second conductor layer 32 thereon produces the optical function part 20. Thereafter, the silicon wafer W is cut for each fine structure part 24 (i.e., for each optical function part 20), whereby a plurality of SERS elements 2 are made. The first and second conductor layers 31, 32 may also be formed after cutting the silicon wafer W into chips.

As explained in the foregoing, this method for manufacturing the SERS element 2 initially forms the first conductor layer 31 on the front face 21a of the substrate 21 and the fine structure part 24 by the first vapor deposition method having a relatively low anisotropy. As a consequence, the first conductor layer 31 is formed on the substrate 21 and the fine structure part 24 so as to continuously cover the front face 21a of the substrate 21 and the fine structure part 24 with a uniform thickness. On the other hand, this method forms the second conductor layer 32 on the first conductor layer 31 by the second vapor deposition method having a relatively high anisotropy. This causes conductor particles to deposit unevenly, thereby forming the second conductor layer 32 having such grooves 33a as to form nanogaps.

Therefore, even if gases and the like are generated from foundation parts such as the substrate 21 and fine structure part 24, the first conductor layer 31 can reduce the influence of the gases and the like on the second conductor layer 32. Hence, this method makes it unnecessary to restrict materials constituting the substrate 21, fine structure part 24, and the like to those which do not generate gases and the like causing contamination in the second conductor layer 32, whereby the degree of freedom in design can be restrained from lowering when manufacturing the SERS element 2.

By using the second vapor deposition method having a relatively high anisotropy, this method forms the second conductor layer 32 on the first conductor layer 31 produced on the fine structure part 24 having a plurality of pillars 27. Therefore, as mentioned above, the second conductor layer 32 is formed with the protrusions 34 corresponding to the pillars 27 in the fine structure part 24 and the base part 33 formed with the grooves 33a surrounding the pillars 27. As a result, the SERS element 2 having the first and second gaps G1, G2 functioning as nanogaps within each groove 33a can be manufactured.

Since this method forms the second conductor layer 32 by the second vapor deposition method having a relatively high anisotropy, there may be a case where the second conductor layer 32 is hardly formed on the side face 27b of the pillar 27. However, since the first conductor layer 31 has been formed beforehand on the side face 27b of the pillar 27 by the first vapor deposition method even in such a case, a nanogap is securely formed between the conductor layer (the base part 33 of the second conductor layer 32) on the surface 25a of the support part 25 and the conductor layer (first conductor layer 31) on the side face 27b of the pillar 27.

This method forms the second conductor layer 32 by depositing on the first conductor layer 31 the same conductor particles as those of the first conductor layer 31. This restrains the agglomeration of conductor particles from becoming positionally uneven when constructing the second conductor layer 32 and forms uniform agglomerates (particles), thereby making it possible to produce nanogaps stably. When directly depositing conductor particles in foundation parts such as the front face 21a of the substrate 21 and the fine structure part 24, agglomeration may vary depending on compatibility between the material for the foundation parts and the conductor material, thereby hindering particles from being formed evenly.

Since the foundation for the second conductor layer 32 is the first conductor layer 31 made of the same material, favorable nanogaps can be formed stably even when no particles are formed on the second conductor layer 32. That is, this method is easy to form the second conductor layer 32 into a desirable shape regardless of whether particles are formed or not.

Figure 12:
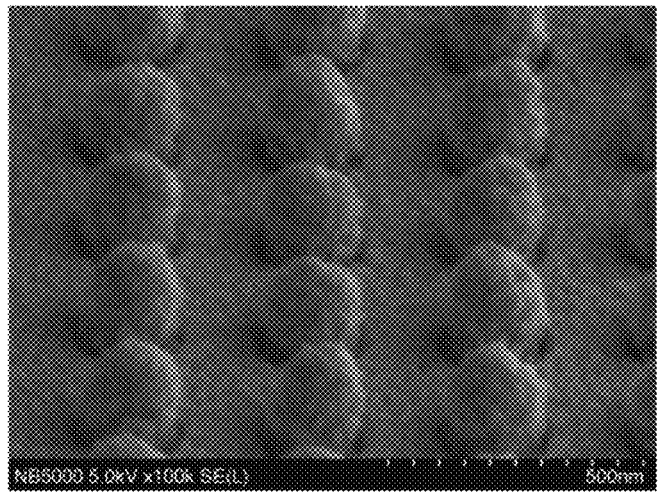
FIG. 12 is a SEM photograph of a fine structure part in the surface-enhanced Raman scattering element of an example.

An example of the SERS element will now be explained. FIG. 12 is a SEM photograph of an optical function part in the SERS element of the example (a SEM photograph capturing the optical function part in a direction tilted by 30° from a direction perpendicular to the surface of the substrate). In this example, Au is deposited by sputtering as the first conductor layer with a thickness of 50 nm and then by evaporation method as the second conductor layer with a thickness of 50 nm. As illustrated in FIG. 12, it is seen in the SERS element of the example that grooves are formed in the base part of the second conductor layer so as to surround pillars of the fine structure part, that end parts of protrusions of the second conductor layer are located within the grooves, and that a number of gaps favorably functioning as nanogaps are formed in the grooves.

The following is a specific method for making the SERS element of this example. First, using a mold in which holes, each having a hole diameter of 120 nm and a hole depth of 180 nm, were arranged in a square lattice at a hole interval (distance between center lines of holes adjacent to each other) of 360 nm, a resin on a substrate made of glass was molded by nanoimprinting, so as to produce a fine structure part. In thus produced fine structure part, the pillars had a diameter of 120 nm, a height of 150 nm, and a pillar pitch (distance between center lines of pillars adjacent to each other) of 360 nm.

Next, Au was deposited on the produced fine structure part by sputtering as the first conductor layer by 50 nm. In this sputtering, Au sputter particles (conductor particles) deposit on the fine structure part while colliding against an Ar plasma gas and thus pile up uniformly with respect to structures such as pillars. For improving the adhesion of the first conductor layer, Ti may be vapor-deposited as a buffer layer under Au, and thereafter Au may be deposited as the first conductor layer on the buffer layer.

Subsequently, Au was deposited by resistance heating vacuum vapor deposition as the second conductor layer by 50 nm. In this vapor deposition, Au is evaporated and deposited in a vacuum and thus is radially linearly vapor-deposited (piled up) from an evaporation source. This produces the SERS element of the example.

Figure 13:
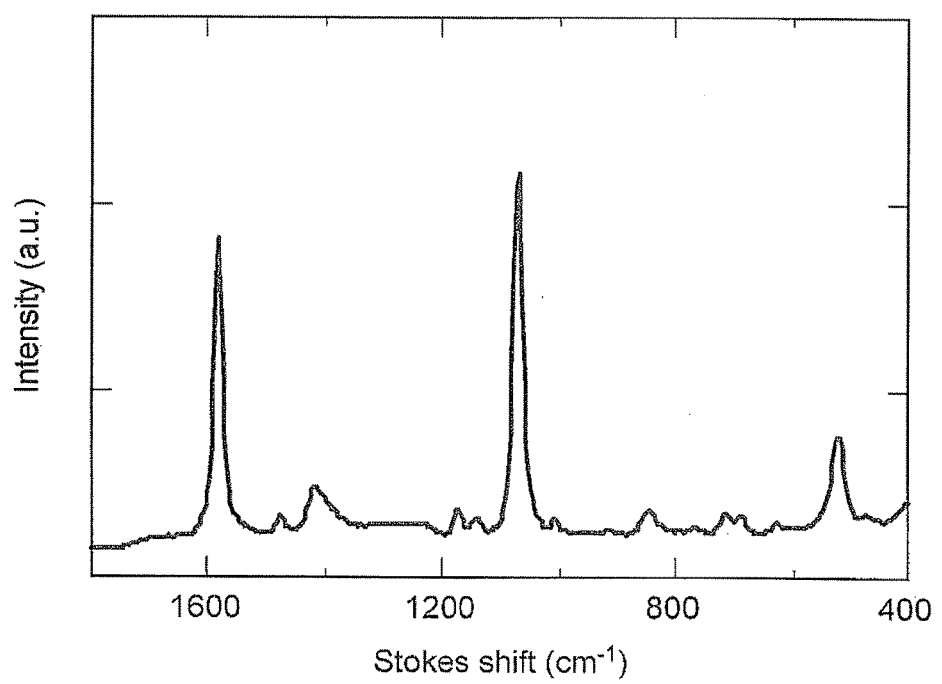
FIG. 13 is a graph illustrating a relationship between Stokes shift and signal intensity concerning the surface-enhanced Raman scattering element of the example.

FIG. 13 is a graph illustrating a relationship between Stokes shift and signal intensity concerning the surface-enhanced Raman scattering element of this example resulting from Raman spectrometry carried out as follows. That is, the SERS element of the example was dipped in an ethanol solution of mercaptobenzonic acid (1 mM) for two hours, then rinsed with ethanol, and dried with a nitrogen gas, so that a sample was arranged on the optical function part of the SERS element. The sample was subjected to Raman spectrometry with excitation light having a wavelength of 785 nm. This resulted in a SERS spectrum of mercaptobenzonic acid as illustrated in FIG. 13, whereby an enchancing effect for surface-enhanced Raman scattering was seen.

While an embodiment of one aspect of the present invention is explained in the foregoing, one aspect of the present invention is not limited to the above-mentioned embodiment. For example, the arrangement structure of the pillars 27 may be one dimensional instead of two dimensional, a triangle lattice instead of a square lattice, or non-periodic. The cross-sectional form of the pillars 27 is not limited to circles, but may be ellipses or polygons such as triangles and quadrangles. As a method for forming the fine structure part 24 on the front face 21a of the substrate 21, thermal nanoimprinting, electron beam lithography, photolithography, and the like may be used instead of the above-mentioned nanoimprinting. The grooves 33a may also be formed so as to surround the pillar 27 in ring forms (such as ellipses) other than circles. The groove 33a may not be formed so as to surround the pillar 27 continuously but intermittently in a state divided into a plurality of regions. Thus, without being restricted to those mentioned above, various materials and forms can be employed for constituents of the SERS element 2.

When attention is focused on a pair of projections (those corresponding to the pillars 27) adjacent to each other, the width of the gap formed by the base part and the protrusion (and the base part and first conductor layer) is smaller than the distance between the conductor layer (e.g., second conductor layer) formed on the outer surface of one projection and that formed on the outer surface of the other projection. This can easily and stably form such a narrow gap (gap favorably functioning as a nanogap) as to be unattainable by the configuration of the fine structure part alone.

The fine structure part 24 may be formed on the front face 21a of the substrate 21 either indirectly with the support part 25, for example, interposed therebetween as in the above-mentioned embodiment or directly. The conductor layer 23 (e.g., first conductor layer) may be formed on the fine structure part 24 either indirectly with a layer such as a buffer metal (Ti, Cr, or the like) for improving the adhesion of a metal to the fine structure part 24, for example, interposed therebetween or directly.

The total thickness of the first conductor layer 31 and base part 33 may be greater than the height of the pillars 27 (projections). In this case, there are no pillars 27 in the parts protruding from the base part 33 in the protrusions 34 of the second conductor layer 32, so that the protrusions 34 are harder to be affected by deformations in the pillars 27 due to thermal expansion and the like, whereby the form of the protrusions 34 is stabilized. As a consequence, the first gap G1 formed by the base part 33 and protrusion 34 favorably functions as a nanogap where electric fields are locally enhanced. Also, as compared with the case without the pillars 27 per se, the conductor layer (constituted by the first and second conductor layers 31, 32) is harder to peel from the fine structure part 24, whereby the form of the conductor layer 23 is stabilized.

Evaporation method may also be used as the first vapor deposition method for forming the first conductor layer 31. In this case, a substrate rotation mechanism (e.g., revolving and rotating planetary members) of a vapor deposition system, the degree of vacuum in a chamber, and the like may be adjusted in order for the first vapor deposition method to have a relatively low anisotropy, i.e., in order for the conductor particles to have relatively random incident directions.

INDUSTRIAL APPLICABILITY

One aspect of the present invention can provide a surface-enhanced Raman scattering element which can stably form a nanogap while being able to restrain the degree of freedom in design from lowering and a method for manufacturing the surface-enhanced Raman scattering element.

REFERENCE SIGNS LIST

2: SERS element (surface-enhanced Raman scattering element); 21: substrate; 21a: front face (principal surface); 24: fine structure part; 27: pillar (projection); 31: first conductor layer; 32: second conductor layer, 33: base part; 33a: groove; 34: protrusion; 34a: end part.

The invention claimed is:
1. A surface-enhanced Raman scattering element comprising:
   a substrate having a principal surface;
   a fine structure part, formed on the principal surface, having a plurality of projections;
   a first conductor layer formed on the principal surface and fine structure part so as to cover the principal surface and fine structure part continuously; and
   a second conductor layer formed on the first conductor layer so as to form a plurality of gaps for surface-enhanced Raman scattering;
   wherein the first and second conductor layers are constituted by the same material,
   a thickness variability of the second conductor layer is greater than a thickness variability of the first conductor layer; and
   the second conductor layer is formed with a gap on a part where no gap is formed in the first conductor layer.

2. A surface-enhanced Raman scattering element according to claim 1, wherein the second conductor layer has a base part formed along the principal surface and a plurality of protrusions protruding from the base part in respective positions corresponding to the projections;
   wherein the base part is formed with a plurality of grooves surrounding the respective projections when seen in the projecting direction of the projections; and
   wherein the gaps are formed at least within the grooves.

3. A surface-enhanced Raman scattering element according to claim 2, wherein the gap includes at least one of a first gap formed within the groove by the base part and the protrusion and a second gap formed within the groove by the base part and the first conductor layer.

4. A surface-enhanced Raman scattering element according to claim 2, wherein the grooves extend like rings so as to surround the respective projections when seen in the projecting direction of the projections.

5. A surface-enhanced Raman scattering element according to claim 2, wherein the protrusion has a form constricted at an end part on the substrate side.

6. A surface-enhanced Raman scattering element according to claim 2, wherein a part of the protrusion located within the groove corresponding thereto is in an agglomerated state.

7. A surface-enhanced Raman scattering element according to claim 2, wherein the base part bulges along an outer edge of the groove.

8. A surface-enhanced Raman scattering element according to claim 2, wherein the base part and the protrusion are connected to each other at the deepest part of the groove.

9. A surface-enhanced Raman scattering element according to claim 2, wherein the base part and the protrusion are separated from each other at the deepest part of the groove.

10. A surface-enhanced Raman scattering element according to claim 1, wherein the projections are arranged periodically along the principal surface.

11. A method for manufacturing a surface-enhanced Raman scattering element, the method comprising:
   a first step of forming a fine structure part having a plurality of projections on a principal surface of a substrate;
   a second step of forming a first conductor layer on the principal surface of the substrate and the fine structure part by a first vapor deposition method; and
   a third step of forming a second conductor layer for surface-enhanced Raman scattering on the first conductor layer by a second vapor deposition method;
   wherein the first and second conductor layers are constituted by the same material;
   wherein the second vapor deposition method has an anisotropy higher than that of the first vapor deposition method,
   a thickness variability of the second conductor layer is greater than that a thickness variability of the first conductor layer; and the second conductor layer is formed with a gap on a part where no gap is formed in the first conductor layer.

* * * * *